US006160131A

United States Patent [19]
Lin et al.

[11] Patent Number: 6,160,131
[45] Date of Patent: *Dec. 12, 2000

[54] SCALABLE METHOD FOR THE ISOLATION OF ANTI-HIV AGENTS FROM THE TROPICAL PLANT CALOPHYLLUM

[75] Inventors: Yuh-Meei Lin, Naperville; Herbert M. Anderson, Woodridge; Tuah R. Jenta, Chicago; Michael J. Williams, Ottawa; Michael T. Flavin, Darien; Ze-Qi Xu, Naperville, all of Ill.

[73] Assignee: Sarawak Medichem Pharmaceuticals, Inc., Lemont, Ill.

[*] Notice: This patent is subject to a terminal disclaimer.

[21] Appl. No.: 09/213,192

[22] Filed: Dec. 17, 1998

Related U.S. Application Data
[60] Provisional application No. 60/068,251, Dec. 19, 1997.

[51] Int. Cl.$^7$ .................. C07D 311/78; C07D 407/14

[52] U.S. Cl. .................................................. 549/277

[58] Field of Search ............................. 549/277

[56] References Cited

U.S. PATENT DOCUMENTS
5,859,049  1/1999  Boyd et al. .

FOREIGN PATENT DOCUMENTS
WO 93/20082  10/1993  WIPO .
WO 94/14789   7/1994  WIPO .
WO 94/28000  12/1994  WIPO .

OTHER PUBLICATIONS

Palmer, C.J. et al., Synthesis of the Calophyllum Coumarins, Tetra. Lett., vol. 35 (30), 1994 5363–66.
Patil et al., J. Med. Chem., 36(26), pp. 4131–38, 1993.
Stout, G.M.; Stevens, K.L.J. Org. Chem. 1964, 29, 3604–3609.
Soejarto, D.D.; Ismawi, O.; Kadushin, M.R.; Lee, H.S. 38$^{th}$ Annual Meeting of the American Society of Pharmacognosy, The University of Iowa, Jul. 26–30, 1997, Abstract P94.
Chaturvedi, A.K. et al., "Anticonvulsant and Antiinflammatory Activity of Natural Plant Coumarins and Triterpenoids," Research Comm. Chem. Path. and Pharm. vol. 9 (1), Sep. 1974, pp. 11–22.
Chenera, B. et al., "Total Synthesis of (±)–Calanolide A, a Non–Nucleoside Inhibitor of HIV–1 Reverse Transcriptase," J. Org. Chem., vol. 58, 1993, pp. 5606–5606.
Games, D. E., et al, "Identification of 4–Phenyl and 4–Alkylcoumarins in Mammea Americana L., Mammea Africana G. Dow, and Calophyllum Inophyllum by Gas Chromatography—Mass Spectometry," Tetra. Lett. No. 31, 1972, pp. 3187–3190.
Gunsakera, S.P. et al., "Chemical Investigation of Ceylonese Plants. Part 27, Extractives of Calophyllum cuneifolium Thw. and Calophyllum soulattri Burm. f. (Guttiferae)" J.C.S. Perkin I, 1977 pp. 1505–1511.
Gunsakera, S.P. et al, "Chemical Investigation of Ceylonese Plants. Part XVI, Extractives of Calopyllum cordato–oblongum Thw. (Guttiferae)," J.C.S Perkin I, 1975, pp. 2215–2220.
Gustafson, K.R. et al., "Calanone, A Novel Coumarin form Calophyllum Teysmannii," Tetra. Lett., vol. 35, No. 32, 1994, pp. 5821–5824.
Kashman, Y. et al., "Additions and Corrections: The Calanolides, a Novel HIV–Inhibitory Class of Coumarin Derivatives from the Tropical Rainforest Tree, Calophyllum lanigerum," J. Med. Chem. vol. 36, 1993, p. 1110.
Kawazu, K. et al., "Piacicidal Constituents of Calophyllum inophyllum," Plant Biochem. vol. 78, 1973, p. 13747 (abstract).
Somanathan, R. et al., "Chemical Investigation of Ceylonese Plants. Part VIII, Trapezifoli–xanthone, a New Di–isoprenylated Xanthone from the Bark of Calophyllum trapezifolium Thw. (Guttiferae)," J.C.S. Perkins I, 1974, pp. 2515–2517.
Deshapande, P.P.; Tagliaferri, F.; Victory, S.F.; Yan, S.; Baker, D.C.J. Org. Chem 1995, 60, 2964–2965.
Gunasekera, S.P.; Jayatilake, G.S.; Selliah, S.S.; Sultanbawa, M.U.S.J. Chem. Soc. Perkins Trans. I 1977, 1505–1511.
Xu, Z.Q.; Creagh, T.; Ruckle, J.; Giltner, J.; Frank, P.; Tolkert, D.; Flavin, M., Preliminary Clinical Safety and Pharmacokinetics Profile of ±–Calanolide A, a Naturally Occurring NNRIT. In the work of 12$^{th}$ World AIDS Conference, Geneva, Jun. 28–Jul. 3, 1998, pp. 403–407.
Kashman, Y.; Gustafson, K.R.; Fuller, R.W.; Cardellina, J.H., II; McMahon, J.B.; Currens, M.J.; Buckheit, R.W., Jr.; Hughes, S.H.; Cragg, G.M.; Boyd, M.R.; The Calanolides, a Novel HIV–Inhibitory Class of Coumarin Derivatives from the Tropical Rainforest Tree, Calophyllum lanigerum. J. Med. Chem. 1992, 35, 2735–2743.
Flavin, M.T.; Rizzo, J.D.; Khilevich, A.; Kucherenko, A.; Sheinkman, A.K.; Vilaychack, V.; Lin, L.; Chen, W.; Mata, E.; Pengsuparp, T.: Pezzuto, J.M.; Hughes, S. H.; Flavin, T.M.; Cibulski, M.; Boulanger, W.A.; Shone, R.L.; Xu, Z.–Q.J. Med. Chem. 1996 39, 1303–1313.

(List continued on next page.)

Primary Examiner—Joseph McKane
Assistant Examiner—Taofiq A. Solola
Attorney, Agent, or Firm—McDonnell Boehnen Hulbert & Berghoff

[57]  ABSTRACT

An efficient and scalable method is reported for the isolation of costatolide (2), an HIV-1-specific nonnucleoside reverse transcriptase inhibitor (NNRTI), from the latex of Calophyllum plants such as *C. teysmannii var. inophylloide*. An overall yield of 10.6% of costatolide, with a purity of 96%, was obtained by repetitive recrystallization of the latex from a single organic solvent after the oily material was removed by treatment with hexane. A second major component of the latex, soulattrolide (3), another HIV-1 NNRTI, was also isolated. Both compounds were characterized by spectroscopic and chromatographic analyses and their in vitro anti-HIV activities were also confirmed. The results suggest that sufficient supplies of costatolide can be obtained in a relatively low-cost manner from natural sources.

23 Claims, No Drawings

OTHER PUBLICATIONS

Curren, M.J.; Gulakowski, R.J.; Mariner, J.M.; Moran, R.A.; Buckheit, R.W., Jr.; Gustafson, K.R.; McMahon, J.B.; Boyd, M.R.J. Pharmacol. Exp. Ther., 1996, 279, 645–651.

Currens, M.J.; Mariner, J.M.; McMahon, J.B.; Boyd, M.R.J. Pharmacol. Exp. Ther. 1996, 279, 652–661.

Cardellina, J.H., II; Bokesch, H.R.; McKee, T.C.; Boyd, M.R., *Bioorg. Med. Chem. Lett*. 1995, 5, 1011–1014.

Fuller, R.W.; Bokesch, H.R.; Gustafson, K.R.; McKee, T.C.; Cardellina J.H., II; McMahon, J.B.; Cragg, G.M.; Soejarto, D.D.; Boyd, M.R. Bioorg & Med. Chem. Letters 1994, 4, 1961–1964.

Pengsuparp, T.; Serit, M.; Hughes, S.H.; Soejarto, D.D.; Pezzuto, J.M.J. Nat. Prod. 1996, 59, 839–842.

Boyer, P.L.; Currens, M.J.; McMahon, J.B.; Boyd, M.R.; Hughes, S.H.J. Virol. 1993, 67, 2412–2420.

Hizi, A.; Tal, R.; Shaharabany, M.; Currens, M.J.; Boyd, M.R.; Hughes, S.H.; McMahon, J.B. Antimicrob. Agents Chemother. 1993, 37, 1037–1042.

Buckheit, R.W., Jr.; Fliakas–Boltz, V.; Decker, W.D.; Roberson, J.L.; Pyle, C. A.; White, E.L.; Bowdon, B.J.; McMahon, J.B.; Boyd, M.R.; Bader, J.P.; Nickell, D.G.; Barth, H.; Antonucci, T.K. Antiviral Res. 1994, 25, 43–56.

Buckheit, R.W., Jr.; Fliakas–Boltz, V.; Decker, W.D.; Roberson, J.L.; Stup, T.L.; Pyle, C.A.; White, E.L.; McMahon, J.B.; Currens, M.J.; Boyd, M.R.; Bader, J.P. Antiviral Res. 1995, 26, 117–132.

Buckheit, R.W., Jr.; Fliakas–Boltz, V.; Yeagy–Bargo, S.; Weislow, O.; Mayers, D.L.; Boyer, P.L.; Hughes, S.H.; Pan, B.–C.; Chu, S.–H.; Bader, J.P. Virology 1995, 210, 186–193.

Buckheit, R.W., Jr.; Kilinjerski, T.L.; Fliakas–Boltz, V.; Russell, J.D.; Stup, T.L.; Palansch, L.A.; Brouwer, W.G.; Dao, D.C.; Harrison, W.A.; Schultz, R.J.; Bader, J.P.; Yang, S.S. Antimicrob. Agents Chemother. 1995, 39, 2718–2727.

Bandara, et al., "Two Chemically Distinct Groups of *Calophyllum* Species from Sri Lanka," Phytochemistry, vol. 25 (2), (1986), pp. 425–428.

Dahanayake, et al., "Chemical Investigation of Cylonese Plants; Extractives of *Calophyllum thwaitesii* Planch and Triana and *Calophyllum walkeri* Wight (Guttiferae)," *J.C.S. Perkin I*, (1974) pp. 2510–2514.

Dharmaratne, et al, "Triterpenoids and Coumarins from the Leaves of *Calophyllum Cordato–Oblongum*," Phytochemistry vol. 24 (7) (1985) pp. 1553–1556.

Dharmaratne, et al, "Xanthones from Roots of Three *Calophyllum* Series," *Phytochemistry* vol. 25 (8) (1986) pp. 1957–1959.

Gautier, et al., "Structure of Calophynic Acid, a Novel Constituent of *Calophyllium Inophyllum.*," *Tetrahedron Letters*, No. 27, (1972) pp. 2715–2718.

Gunatilaka, et al. "Terpenoid and Biflavonoid Constituents of *Calophyllum calaba* and *Garcinia spicata* from Sri Lanka," *Phytcochemistry* vol. 23 (1) (1984) pp. 323–328.

Gustafson, et al., "AIDS–Antiviral Natural Products Research at the U.S. National Cancer Institute," *Natural Products as Antiviral Agents* Chu et al, eds., (Plenum Press, New York 1992).

Gustafson, et al., "A Nonpromoting Phorbol from the Samoan medicinal Plant Ho, alanthus Nutans Inhibits Cell Killng by HIV–1," *J. Med. Chem.* vol. 35, (1992) pp. 1978–1986.

Kumar et al., "Calocalabaxanthone, The Putative Isoprenyl Precursor of Calabaxanthone from *Calophyllum Calaba,*" *Phytochemistry*, vol. 21 (1982) (1982), pp. 807–809.

Mabberly, *The Plant Book*, (Cambridge University Press 1987) p. 92.

Merigan, "Treatment of AIDS with Combinations of Antiretoviral Agents," *Amer. J. Med.* vol. 90, (1991), pp. 4A 8S–17S.

Pauwels, et al, "Potent and Selective Inhibition of HIV–1 Replication in Vitro by a Novel Series of TIBO Derivatives," *Nature*, vol. 343, (1990), pp. 470–474.

Samaraweera, et al, "Calozeylanic Acid, a New Bark Acid from Three *Calophyllum* Species," *Tetrahedron Letters* vol. 22, (1981), pp. 5083–5086.

Soejarto, et al., "Challenges in Developing a New Drug from Tropical Rain Forest Plants," *Proceedings of the Symposium of the Industrial Utilization of Tropical Plants and the Conservation of Biodiversity*, Enugu, Nigeria Feb. 14–19, 1984.

Stout, et al., "Calophyllum Products III., The Structures of Blancoic Acids" *J. Org. Chem.* vol. 33, (1968) pp. 4185–4190.

Stout, et al. "The Structure of Costatolide" *J. Org. Chem.* vol. 29, (1964) pp. 3604–3609.

SCALABLE METHOD FOR THE ISOLATION OF ANTI-HIV AGENTS FROM THE TROPICAL PLANT CALOPHYLLUM

CROSS-REFERENCE

This application is a continuation-in-part of U.S. patent Ser. No. 60/068,251, filed Dec. 19, 1997.

FIELD OF THE INVENTION

The present invention relates to an improved method for isolating purified costatolide and soulattrolide from the trunkbark latex of Calophyllum plants.

BACKGROUND OF THE INVENTION

A series of polycyclic coumarins were isolated, through the natural products screening program at the National Cancer Institute, from several tropical plants of the genus Calophyllum in Sarawak, Malaysia. These natural products, including (+)-calanolide A (1, NSC 650886),[1–4] (–)-calanolide B (costatolide) (2, NSC 661122),[1,5] and soulattrolide (3),[6] were identified as HIV-1- specific nonnucleoside reverse transcriptase inhibitors (NNRTIs)[1,2,7–9] with unique drug-resistance profiles.[10–13] (+)-Calanolide A (1), the most potent compound in the series, was selected for further development and is currently in clinical trials to evaluate its safety and pharmacokinetics of single and multiple doses in normal healthy volunteers.[18] After oral administration, (+)-calanolide A (1) was generally well tolerated and no patterns indicative of a safety concern were observed.[18] Plasma concentrations of (+)-calanolide A(1) in humans were higher than anticipated from animal data and it appeared that therapeutic levels can be achieved in humans.[18]. Because of our ongoing interest in developing (+)-calanolide A (1) and related compounds, we were interested in developing other (+)-calanolide, A analogues, such as costatolide (2) as a possible alternative to calanolide A(1).

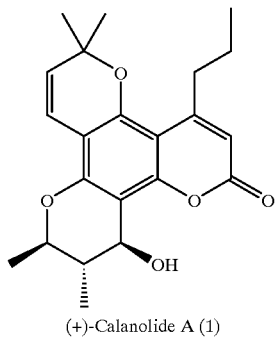

(+)-Calanolide A (1)

-continued

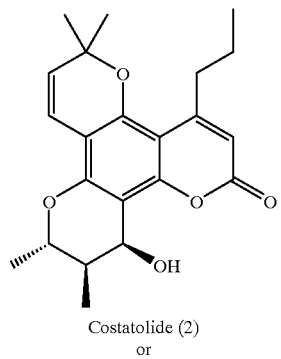

Costatolide (2)
or
(-)-Calanolide B

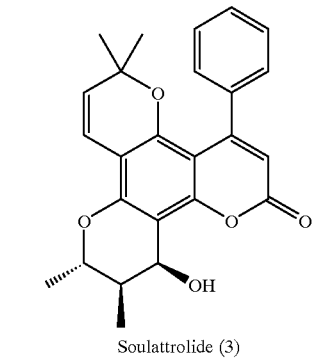

Soulattrolide (3)

Unlike (+)-calanolide A (1), which is extremely limited from natural sources, with the best yields obtained thus far being approximately 1 mg/g extract,[6] costatolide (2) is rich in the latex of *Calophyllum teysmannii*, a very abundant plant species.[6] A yield of 48% costatolide (2) was isolated from the latex extractables by repetitive chromatographies including preparative HPLC.[6] Since latex harvests could, in theory, be sustained over an extended period of time and would not be destructive to the plant, sufficient supplies of costatolide (2) could be obtained from natural sources for preclinical and clinical development, and possible commercialization,[14] providing that a scalable isolation method could be developed which is superior to the synthetic approaches[2,15] and earlier isolation approaches[6,19] in terms of overall yield, cost effectiveness, and environmental implications. For instance, U.S. Pat. No. 5,591,770 describes the isolation of costatolide and soulattrolide in small quantities by HPLC, a tedious and high cost method which is not suitable for industrial production of costatolide and soulattrolide.

SUMMARY OF THE INVENTION

The present invention relates to an improved efficient and scalable method for the isolation of costatolide (2) from the trunkbark latex of Calophyllum plants such as *C. teysmannii*. The method can also be applied to extracting and isolating a second major component of the latex, soulattrolide (3), another HIV-1 NNRTI.

According to the method of the invention, the latex was initially treated with a non-polar solvent, e.g., hexane, to extract preferably non-costatolide materials, leaving behind a solid residue of crude costatolide. The resulting crude costatolide was then recrystallized from a aprotic polar solvent, e.g., acetone, repeatedly to produce a final costatolide product that was 96% pure. If desired, additional costatolide as well as soulattrolide can be recovered from the mother liquors and purified via recrystallization. The method of the invention is economical and useful for isolation of purified costalide and soulattrolide in kilogram quantities from latex.

DETAILED DESCRIPTION OF THE INVENTION

All references, patents and published patent applications cited herein are incorporated by reference in their entirety.

The latex starting material may be obtained from Calophyllum plants such as *C. teysmannii* Miq. and *C. teysmannii* Miq. var. *Inophylloide* (ing) P. F. Stevens and *C. lanigerum* var. *austrocoriaceum* (T. C. Whitmore) P. F. Stevens, which are found typically in Southeast Asia, Sri Lanka, and Northern Australia.

*C. teysmannii* latex, provided by the Forest Research Centre of Sarawak, Malaysia, was isolated according to described procedures[19] and was analyzed by quantitative high performance liquid chromatography (HPLC) analysis. The results indicated that the latex consisted of costatolide (~37 %) and soulattrolide (~23 %), along with other unidentified components. A preliminary solubility study revealed that the latex was soluble in almost all organic solvents at room temperature with the following order: $CH_2Cl_2$ (400 mg/mL)>$CH_2Cl_2$/MeOH (1:1)≅AcOEt (~200 mg/mL)>$CH_2Cl_2$/AcOEt (1:1) (50 mg/mL)>acetone≅MeOH (40 mg/mL)>EtOH (30 mg/mL)>hexane (20 mg/mL). Hence, for a preliminary extraction of mostly non-costatolide components from the latex, it is preferred that the latex be treated with any suitable solvent that least solubilizes the latex such as a non-polar solvent, e.g., hexane and heptane.

The amount of solvent used relative to latex ranges between about 5 L/Kg latex and about 13 L/Kg latex, preferably about 8L/Kg latex. The preliminary extraction of the latex starting material may be conducted under solvent reflux conditions or preferably at room temperature. Thus, treatment of the latex with hexane dissolved approximately 50% of the latex by weight, resulting in an off-white solid residue which contained approximately 50% costatolide (2) as determined by quantitative HPLC analysis. Additional amounts of crude costatolide may be obtained by allowing the hexane solution to stand at room temperature for several days. The resulting crude costatolide was then collected and pooled with the residue.

The solid residue is then dissolved in a suitable solvent, e.g., $CH_2Cl_2$ or acetone, to remove any insoluble bark debris by filtration of the resulting solution through a cotton cloth, glass cotton or other suitable filtering material. In practicing the invention, the solvent acetone is preferred because the resulting acetone solution was more convenient to filter than the $CH_2Cl_2$ solution.

After removal of solvent by any suitable method such as reduced pressure evaporation or distillation, the solid product obtained is recrystallized repeatedly from a suitable solvent, e.g. a polar aprotic solvent such as acetone, t-butylmethyl ether, ethyl acetate or solvent mixtures of acetone/ethyl acetate, ethyl acetate-t-butylmethyl ether, or acetone/t-butylmethyl ether, to produce a final product of costatolide with purity of greater than 96%. In practicing this invention, acetone is the preferred recrystallization solvent for costatolide. Mother liquors containing similar purity levels of costatolide (2) were combined, solvent was removed and the resulting residue was recrystallized from acetone to yield an additional quantity of costatolide (2). It has been observed that each iteration of the recrystallization step resulted in an increase in costatolide (2) purity by an average of 10%, with recovery yield of 40 to 70%. Generally, the purity of the resulting crystalline product was inversely proportional to the recrystallization yield.

In practicing the invention, the appropriate volume (in milliliters) of solvent needed for each recrystallization step ranged between about 5 mL to about 12 mL per grain of solid to be recystallized, preferably about 10 mL of solvent, e.g., acetone, per gram of solid product.

A typical example described in Example No. 1, starting with 1.96 kilograms of latex, is presented in Scheme I. Another batch of 2.64 kilograms of latex yielded similar results. From these two batches, representing a total of 4.60 kilograms of latex, a combined 490 grams of costatolide (2) was obtained with a purity greater than 96% in an overall yield of 10.6%, along with other less pure fractions (Table 1). A higher overall yield could be expected if the less pure fractions were combined and upgraded by silica gel column chromatography, followed by the recrystallization processes described above. During this study, organic solvents employed were hexane (95 L), $CH_2Cl_2$ (25 L), and acetone (45 L). The fraction containing a mixture of costatolide (2) and soulattrolide (3) in a ratio of 1:1 was further purified either by repetitive recrystallization from ethanol (ca. 3–5 times) or by flash silica gel column chromatography followed by recrystallization from ethanol to afford soulattrolide (3) with a purity greater than 96%.

The structures of purified costatolide (2) and soulattrolide (3) were elucidated by MS and 2D-NMR and their physical (mp, [α]D) and spectral data (UV, IR, $^1$H NMR, and $^{13}$C NMR) were identical with those reported in the literature.[1,6,16,17] In addition, the anti-HIV activities of both compounds were also confirmed in the in vitro XTT assay. The isolated costatolide (2) and soulattrolide (3) had $EC_{50}$ values of 0.18 $\mu$M and 0.62 $\mu$M, respectively, in CEM-SS cells against the HIV-1 RF strain.

TABLE 1

Summary of Results Obtained from 4.60 Kilograms of Latex

| Fractions | Purity of Costatolide |
| --- | --- |
| 490 g | >96% |
| 75 g | 90%[a] |
| 129 g | 80%[a] |
| 80 g | 60%[a] |
| 60 g | 50%[a] |
| 917 g | 30–40% |
| 2450 g | oily material |
| 4201 g (total)[b] | |

[a]The remaining major constituent was soulattrolide (3).
[b]The bark debris and volatiles accounted for the loss.

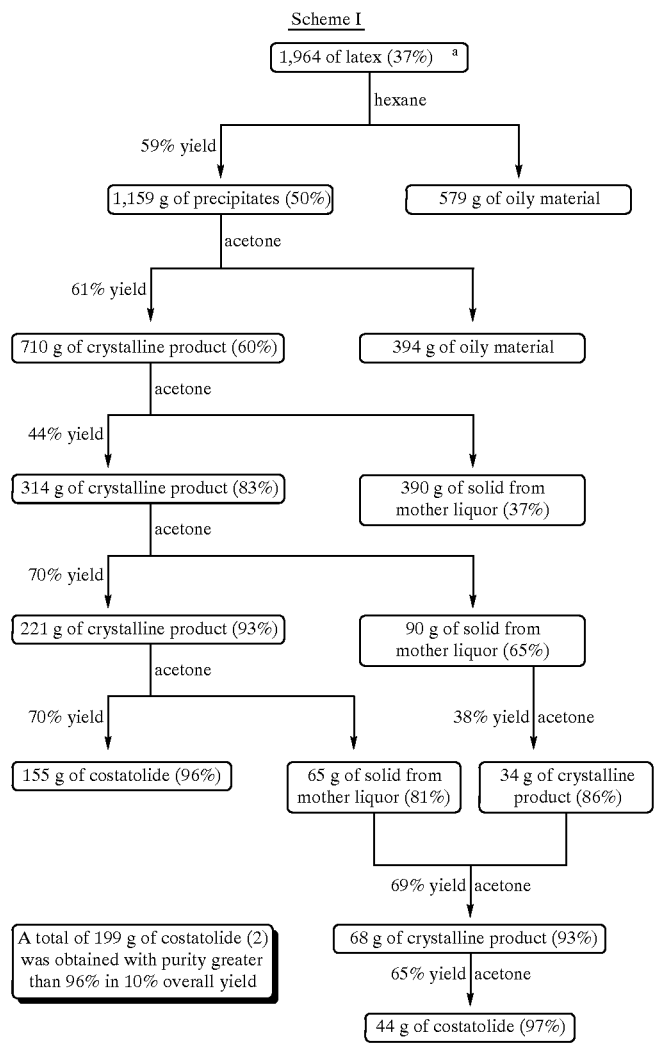

Scheme I

[a] The values in parentheses represent the purity of costatolide (2) determined by quantitative HPLC In summary, an efficient and scalable method has been demonstrated for the isolation of costatolide (2), an anti-HIV agent, from the latex of *C. teysmannii*. It is therefore possible that sufficient supplies of 2 could be obtained in a relatively low-cost manner from natural sources. The purified 490 grams of 2 will be utilized for further preclinical development of this compound.

Another anti-HIV agent, soulattrolide (3), has also been isolated utilizing this process, using the mother liquor fractions that were enriched with soulattrolide, preferably the fractions containing a weight ratio of at least 1:1 (w/w) soulattrolide to costatolide. The soulattrolide, however, was preferably recrystallized from any suitable polar solvent such as ethanol, methanol, diethyl ether, or solvent mixtures such as diethylether with ethanol or methanol. In practicing this invention, the preferred recrystallization solvent for soulattrolide is ethanol.

EXPERIMENT NO. 1: Isolation of Costatolide (2) from Latex

Plant Material. The latex of *Calophyllum teysmannii* var. *inophlylloide* was collected[19] at Kubah N. P. and Bedaun (Pueh F. R.), Kuching Division, Sarawak, Malaysia.

General Experimental Procedure. Optical rotations were measured on a Perkin Elmer Model #241 Polarimeter Serial #4677. NMR spectra were recorded with a Varian Gemini spectrometer (300 MHz for $^1$H and 75.5 MHz for $^{13}$C) using $CDCl_3$ as solvent. UV spectra were recorded on a Hitachi U-2001 Spectrometer. IR Spectra were acquired on a Perkin Elmer Model Paragon 1000 FT-IR spectrometer, with samples being prepared as KBr pellets. MS were obtained with a Finnigan MAT 90 mass spectrometer. An APCI or ESI probe was used for APCIMS or EIMS spectra. HPLC analyses were performed on a Hitachi HPLC system equipped with a L-4000 H UV detector and L-6000 pump. A normal phase column (B17419 Zorbax, 4.6 mm×25 cm) was purchased from Rockland Technologies, Inc., and the mobile phase was 30% AcOEt in hexane with a flow rate of 1 mL/min.

Treatment of Latex with Hexane.

Method A. at R.T.: Latex (1,964 g) containing approximately 37% costatolide (2) and 23% soulattrolide (3), as determined by quantitative HPLC analysis, was stirred in 15 L of hexane at r.t. for 1 hr. The solid was allowed to settle, and then was filtered through a filter stick by vacuum transfer and washed with hexane (10 L×2). The solid product thus obtained was dissolved in 15 L of $CH_2Cl_2$ and filtered through cotton cloth to remove bark debris. Removal of solvent afforded 1,026 g of a light yellowish solid, with the purity of costatolide (2) being increased to approximately 50%.

The combined greenish yellow hexane solution and washes were concentrated under vacuum. When the volume was reduced to approximately 10 L, precipitates formed, which were collected by filtration to yield an additional 133 g of an off-white solid which contained 30% of 2, resulting in a total of 1,159 g of costatolide-containing solid in a yield of 59% recovered from latex after the hexane treatment. The filtrate was concentrated to dryness to leave a 579 g of greenish oil with less than 3% 2, as determined by HPLC.

Method B. Refluxing: A quantity of 2.64 kg of latex and 15 L of hexane was heated to reflux for one hour. The solid was allowed to settle, and then was filtered through a filter stick by vacuum transfer and washed with hexane (15 L×2) to afford 844 g of an off-white solid containing approximately 50% of costatolide (2). An additional 242 g of a light yellow solid, with 39% of 2, was obtained from the combined hexane solutions after standing at r.t. for one week. The filtrate was concentrated to ⅓ volume and allowed to stand at r.t. for one week to yield 107 g of a pale yellow solid with a purity of 57% of costatolide (2). A total of 1,080 g of oily material was obtained after concentration from all the filtrates, which had less than 3% 2 as determined by HPLC. The recovery yield of costatolide-containing solid from this batch was 45% after the hexane treatment.

Step 1 Recrystallization to Increase the Purity of 2 from 50% to 60%: An amount of 1,026 g (50% pure) of the off-white solid was refluxed in 10 L of acetone until a clear brown solution was obtained, which was filtered hot through a glass fritted funnel under vacuum. The resulting solution was allowed to stand at r.t. for 2 days. The resulting solid was collected and washed with hexane to yield 678 g (66% yield) of a crystalline product, with the purity of 2 being increased to 60%. The filtrate was concentrated to ½ the volume and 50 g of precipitate, with a purity of 32% of 2 were collected through filtration. The filtrate was evaporated to dryness to afford 250 g of oil without detectable amounts of 2.

Step 2 Recrystallization to Increase the Purity of 2 from 60% to 80%: An amount of 678 g (60% pure) of the solid obtained above was recrystallized in the same manner described above from 5.5 L of acetone to yield 184 g (27% yield) of crystals with a purity of 82% of 2 and 492 g (50% pure) of material from the mother liquor.

Step 3 Recrystallization to Increase the Purity of 2 from 80% to 90%: An amount of 184 g (82% pure) of the solid obtained above was recrystallized in the same manner described above from 1.9 L of acetone to yield 119 g (65% yield) of crystals with a purity of 93% of 2 and 65 g (50% pure) of material from the mother liquor.

Step 4 Recrystallization to Increase the Purity of 2 from 90% to 96%: An amount of 393 g (93% pure) of the solid was recrystallized in the same manner described above from 2.9 L of acetone to yield 277 g (71%) of crystalline costatolide (2) with purity of 96% and 125 g (82% pure) of material from the mother liquor. Costatolide (2):[1,6,16] mp. 174–175° C. (Lit.[16] 181–182° C.); $[\alpha]_D$ –22.2 (c 0.71, $CHCl_3$) {Lit. $[\alpha]_D$ –19.9 (c 0.42, $CHCl_3$)}; UV ($CHCl_3$) $\lambda_{max}$ (log ε) 222 (4.67), 285 (4.43), 327 (4.10) nm; IR (KBr) $v_{max}$ 3477, 2961, 2931, 1703, 1638, 1584, 1569 $cm^{-1}$; APCI-MS: m/z 371 $(M+H)^+$; $^1H$ NMR: 1.03 (3H, t, J=7.2 Hz, $CH_3$), 1.14 (3H, d, J=6.9 Hz, $CH_3$), 1.43 (3H, d, J=6.3 Hz, $CH_3$), 1.48 (3H, s, $CH_3$), 1.49 (3H, s, $CH_3$), 1.65 (2H, sextet, J=7.2 Hz, $CH_2$), 1.74 (1H, m, H-11), 2.67 (1H, d, J=3.9 Hz, OH), 2.88 (2H, m, $CH_2$), 4.27 (1H, dq, J=6.6, 6.9 Hz, H-10), 4.97 (1H, broad, H-12), 5.53 (1H, d, J=9.9 Hz, H-7), 5.94 (1H, s, H-3), 6.63 (1H, d, J=9.9 $^{13}C$ NMR: 12.5 ($CH_3$), 14.0 ($CH_3$), 18.8 ($CH_3$), 23.2 ($CH_2$), 27.6 ($CH_3$), 27.8 ($CH_3$), 38.2 (C-11), 38.5 ($CH_2$), 61.8 (C-12), 73.0 (C-6), 77.6 (C-10), 103.5 (C-4a), 106.1 (C-8a or C-12a), 106.3 (C-12a or C-8a), 110.3 (C-3), 116.6 (C-8), 126.7 (C-7), 151.4 (C-4b), 153.1 (C-8b or C-12b), 153.9 (C-12b or C-8b), 158.7 (C-4), 161.0 (C=0); Elem. Anal.: C 71.40%, H 7.20%; Calcd. for $C_{22}H_{26}O_5$: C 71.33%, H 7.08%.

Soulattrolide (3): An amount of 20 g of solid obtained from the above acetone recrystallization, which contained approximately 1:1 ratio of costatolide (2) and soulattrolide (3), was subjected to flash silica gel column chromatography (Biotage Flash Column), eluting with a stepwise gradient of AcOEt in hexane: 10% (5L), 15% (10 L), 20% (15 L), and 100% AcOEt (5 L). A volume of 500 mL was collected for each fraction. Fractions 28 and 29 contained soulattrolide (3) (~70 % by HPLC). Crystalline needles (300 mg, 89 % purity of 3) were formed in fraction 29 and collected. The crystals were recrystallized from EtOH twice to afford 170 mg of soulattrolide (3) with a purity of 97 % by HPLC. Soulattrolide (3):[17] mp 200–201° C. (Lit. 201–202° C.); $[\alpha]_D$ –34.2 (c 0.24, $CHCl_3$) {Lit.[17] $[\alpha]_D$ –29.6° ($CHCl_3$)}; UV ($CHCl_3$) $\lambda_{max}$ (log ε) 216 (4.74), 232 (4.53), 286 (4.56), 335 (4.29) nm; IR (KBr) $v_{max}$ 3457, 2862, 1698, 1584, 1366, 1139, 837, 762 $cm^{-1}$; APCIMS m/z 405 $[M+H^+]$; $^1H$ NMR: 0.93 (6H, s, 2 $CH_3$), 1.16 (3H, d, J=7.2 Hz, $CH_3$), 1.44 (3H, d, J=7.2 Hz, $CH_3$), 1.76 (1H, m, H-11), 2.79 (1H, d, J=3.6 Hz, OH), 4.26 (1H, dq, J=6.4, 10.7 Hz, H-10), 4.96 (1H, d, J=3.2 Hz H-12), 5.34 (1H, d, J=9.8 Hz, H-7), 5.94 (1H, s, H-3), 6.51 (1H, d, J=9.8 Hz, H-8), 7.3 (5H, m, $C_6H_5$); $^{13}C$ NMR: 12.4 ($CH_3$), 18.7 ($CH_3$), 26.7 ($CH_3$), 26.8 ($CH_3$), 38.7 (C-11), 61.7 (C-12), 73.0 (C-10), 76.6 (C-6), 103.6 (C-4a), 106.1 (C-8a or C-12a), 106.2 (C-12a or C-8a), 111.7 (C-3), 116.0 (C-8), 127.3 (para- and meta-$C_6H_5$), 127.4 (ortho-$C6H_5$), 127.6 (C-7), 140.1 (ipso-$C_6H5$), 151.2 (C-4b), 153.6 (C-8b or C-12b), 153.9 (C-12b or C-8b), 156.4 (C-4), 160.8 (C=0); Elem. Anal.: C 73.94 %, H 6.10 %, Calcd. for $C_{25}H_{24}O_5$, C 74.24 %, H 5.98%.

EXPERIMENT NO. 2: Isolation of Soulattrolide from enriched mother liquors

Solid material obtained from mother liquor of costatolide recrystallization as described in Experiment No. 1, which contained soulattrolide and costatolide in the weight ratio of about 1:1, was purified via recrystallization (3×) from ethanol to produce solatrrolide (3) of 95.5% purity in a total yield of 41.5% starting from latex.

Step No. 1: Recrystallization to purity of (3) from 49% to 63%: A quantity of 13 g of solid (soulattrolide 49%, costatolide 49%) was dissolved in 260 mL of hot ethanol by refluxing, and filtered. The clear filtrate was let stand at room temperature overnight. The precipatate shown was filtered to produce 9.28 g of off-white crystals with a purity of 63.4% of 3 (yield 71.5%).

Step No. 2. Recrystallization to increase purity of (3) from 63% to 93%: An amount of 9.28 g of solid (soulattrolide 63%, costatolide 33%) was recrystallized in the same manner described above from 250 mL of ethanol to produce 7.04 g of white crystals with a purity of 93% of 3 (yield 75.9%).

Step No. 3. Recrystallization to increase purity of (3) from 93% to 95.5%: An amount of 7.04 g of solid (soulattrolide 93%, costatolide 5.1%) was recrystallized in the same manner described above from 250 mL of ethanol to produce 5.38 g of white crystals with a purity of 95.5% of 3 (yield 76.4%).

REFERENCES (1) Kashman, Y.; Gustafson, K. R.; Fuller, R. W.; Cardellina, J. H., II; McMahon, J. B.; Currens, M. J.; Buckheit, R. W.; Hughes, S. H.; Cragg, G. M.; Boyd, M. R. *J. Med. Chem.* 1992, 35, 2735–2743.

(2) Flavin, M. T.; Rizzo, J. D.; Khilevich, A.; Kucherenko, A.; Sheinkinan, A. K.; Vilaychack, V.; Lin, L.; Chen, W.; Mata, E.; Pengsuparp, T.; Pezzuto, J. M.; Hughes, S. H.; Flavin, T. M.; Cibulski, M.; Boulanger, W. A.; Shone, R. L.; Xu, Z.-Q. *J. Med. Chem.* 1996, 39, 1303–1313.

(3) Currens, M. J.; Gulakowski, R. J.; Mariner, J. M.; Moran, R. A.; Buckheit, R. W., Jr.; Gustafson, K. R.; McMahon, J. B.; Boyd, M. R. *J. Pharmacol. Exp. Ther.* 1996, 279, 645–651.

(4) Currens, M. J.; Mariner, J. M.; McMahon, J. B.; Boyd, M. R. *J. Pharmacol. Exp. Ther.* 1996, 279, 652–661.

(5) Cardellina, J. H., II; Bokesch, H. R.; McKee, T. C.; Boyd, M. R. *Bioorg. & Med. Chem. Letters* 1995, 5, 1011–1014.

(6) Fuller, R. W.; Bokesch, H. R.; Gustafson, K. R.; McKee, T. C.; Cardellina J. H., II; McMahon, J. B.; Cragg, G. M.; Soejarto, D. D.; Boyd, M. R. *Bioorg. & Med. Chem. Letters* 1994, 4, 1961–1964.

(7) Pengsuparp, T.; Serit, M.; Hughes, S. H.; Soejarto, D. D.; Pezzuto, J. M. *J. Nat. Prod.* 1996, 59, 839–842.

(8) Boyer, P. L.; Currens, M. J.; McMahon, J. B.; Boyd, M. R.; Hughes, S. H. *J. Virol.* 1993, 67, 2412–2420.

(9) Hizi, A.; Tal, R.; Shaharabany, M.; Currens, M. J.; Boyd, M. R.; Hughes, S. H.; McMahon, J. B. *Antimicrob. Agents Chemother.* 1993, 37, 1037–1042.

(10) Buckheit, R. W., Jr.; Fliakas-Boltz, V.; Decker, W. D.; Roberson, J. L.; Pyle, C. A.; White, E. L.; Bowdon, B. J.; McMahon, J. B.; Boyd, M. R.; Bader, J. P.; Nickell, D. G.; Barth, H.; Antonucci, T. K. *Antiviral Res.* 1994, 25, 43–56.

(11) Buckheit, R. W., Jr.; Fliakas-Boltz, V.; Decker, W. D.; Roberson, J. L.; Stup, T. L.; Pyle, C. A.; White, E. L.; McMahon, J. B.; Currens, M. J.; Boyd, M. R.; Bader, J. P. *Antiviral Res.* 1995, 26, 117–132.

(12) Buckheit, R. W., Jr.; Fliakas-Boltz, V.; Yeagy-Bargo, S.; Weislow, O.; Mayers, D. L.; Boyer, P. L.; Hughes, S. H.; Pan, B.-C.; Chu, S.-H.; Bader, J. P. *Virology* 1995, 210, 186–193.

(13) Buckheit, R. W., Jr.; Kilnjerski, T. L.; Fliakas-Boltz, V.; Russell, J. D.; Stup, T. L.; Palansch, L. A.; Brouwer, W. G.; Dao, D. C.; Harrison, W. A.; Schultz, R. J.; Bader, J. P.; Yang, S. S. *Antimicrob. Agents Chemother.* 1995, 39, 2718–2727.

(14) Soejarto, D. D.; Ismawi, O.; Kadushin, M. R.; Lee, H. S. 38th Annual Meeting of the American Society of Pharmacognosy, The University of Iowa, Jul. 26–30, 1997, Abstract P94.

(15) Deshapande, P. P.; Tagliaferri, F.; Victory, S. F.; Yan, S.; Baker, D. C. *J. Org. Chem.* 1995, 60, 2964–2965.

(16) Stout, G. M.; Stevens, K. L. *J. Org. Chem.* 1964, 29, 3604–3609.

(17) Gunasekera, S. P.; Jayatilake, G. S.; Selliah, S. S.; Sultanbawa, M. U. S. *J. Chem. Soc. Perkins Trans. I* 1977, 1505–1511.

(18) Xu, Z. Q.; Creagh, T.; Ruckle, J.; Giltner, J.; Frank, P.; Tolkert, D.; Flavin, M., Preliminary Clinical Safety and Pharmacokinetics Profile of (+)-Calanolide A, a Naturally Occurring NNRIT. In the work of of $12^{th}$ World AIDS Conference, Geneva, Jun. 28–Jul. 3, 1998, pp. 403–407.

(19) U.S. Pat. No. 5,591,770, issued Jan. 7, 1997.

What is claimed is:

1. A method for isolating costatolide from latex of a Calophyllum plant comprising the steps of:
   (a) providing latex from a Calophyllum plant;
   (b) extracting latex with a non-polar organic solvent to obtain an extract solution and a solid product;
   (c) recrystallizing the solid product repeatedly with a polar organic solvent to produce crystalline costatolide and mother liquor; and
   (d) recovering the crystalline costatolide.

2. The method according to claim 1, further comprising concentrating the extract solution to obtain additional solid product.

3. The method according to claim 1, further comprising concentrating the mother liquor to obtain additional solid product.

4. The method according to claim 1, wherein debris in the latex is removed prior to step (b).

5. The method according to claim 1, wherein said non-polar organic solvent comprises hexane or heptane.

6. The method according to claim 5, wherein said non-polar organic solvent is hexane.

7. The method according to claim 1, wherein said polar organic solvent is member selected from the group consisting of acetone, t-butylmethyl ether, ethyl acetate and mixtures thereof.

8. The method according to claim 7, wherein said polar organic solvent is acetone.

9. A method for isolating soulattrolide from latex of a Calophyllum plant comprising the steps of:
   (a) providing latex from a Calophyllum plant;
   (b) extracting latex with a non-polar organic solvent to obtain an extract solution and a solid product;
   (c) recrystallizing the solid product repeatedly with a first polar organic solvent to obtain crystalline costatolide and a first mother liquor;
   (d) separating and concentrating the first mother liquor to obtain a second solid product;
   (e) recrystallizing the second solid product repeatedly with a second polar organic solvent to obtain crystalline soulattrolide and a second mother liquor; and
   (f) recovering the crystalline soulattrolide.

10. The method according to claim 9, wherein the second solid product has soulattrolide and costatolide at a weight ratio of about 1:1.

11. The method according to claim 9, further comprising concentrating the extract solution to obtain additional solid product.

12. The method according to claim 9, further comprising concentrating the first mother liquor to obtain additional solid product.

13. The method according to claim 9, wherein debris in the latex is removed prior to step (c).

14. The method according to claim 9, wherein said non-polar organic solvent comprises hexane or heptane.

15. The method according to claim 14, wherein said non-polar organic solvent comprises hexane.

16. The method according to claim 9, wherein said first polar organic solvent is selected from the group consisting of acetone, t-butylmethyl ether, ethyl acetate, and mixtures thereof.

17. The method according to claim 16, wherein said first polar organic solvent is acetone.

18. The method according to claim 9, wherein said second polar organic solvent is selected from the group consisting of ethanol, methanol, diethyl ether and mixtures thereof.

19. The method according to claim 18, wherein said second polar organic solvent is ethanol.

20. The method according to claims 1 or 9 wherein said latex is derived from *Calophyllum lanigerum* Miq.

21. The method according to claims 1 or 9 wherein said latex is derived from *Calophyllum lanigerum* Miq. var. *austrocoriaceum,* (T. C. Whitmore) P. F. Stevens.

22. The method according to claims 1 or 9 wherein said latex is from *Calophyllum teysmannii* Miq.

23. The method according to claims 1 or 9 wherein said latex is derived from *Calophyllum teysmannii* Miq. var. *inophylloide* (King) P. F. Stevens.

* * * * *